United States Patent [19]
Mörmann

[11] Patent Number: 5,939,211
[45] Date of Patent: Aug. 17, 1999

[54] METHOD FOR THE MANUFACTURE OF DENTAL RECONSTRUCTIONS AND BLANK FOR CARRYING OUT THIS METHOD

[75] Inventor: Jeanette Mörmann, Zweiackerstrasse 51, 8053 Zürich, Switzerland

[73] Assignees: Jeanette Mörmann; Marco Brandestini, both of Montagnola, Switzerland

[21] Appl. No.: 08/852,742

[22] Filed: May 7, 1997

[30] Foreign Application Priority Data

May 17, 1996 [CH] Switzerland .......................... 1251/96

[51] Int. Cl.⁶ ...................................................... B32B 7/00
[52] U.S. Cl. .................... 428/542.8; 428/34.5; 428/35.7; 428/36.9; 428/36.91; 428/469; 428/472; 428/701; 428/702; 433/49; 433/201.1; 433/167; 433/197; 433/215; 433/218; 433/222.1; 264/16; 264/17; 264/19
[58] Field of Search ................................ 428/542.8, 469, 428/34.5, 472, 35.7, 701, 36.9, 702, 36.91; 76/28; 264/16, 19, 17, 18, 20; 156/153; 433/49, 229, 223, 215, 218, 40, 201.1, 167, 199.1, 197, 222.1, 202.1, 206; 33/513, 512; 29/592, 896.1

[56] References Cited

U.S. PATENT DOCUMENTS

| | | | |
|---|---|---|---|
| 3,004,343 | 10/1961 | Rydin | 32/13 |
| 4,615,678 | 10/1986 | Moermann et al. | 433/201 |
| 4,970,032 | 11/1990 | Rotsaert | 264/20 |
| 5,151,044 | 9/1992 | Rotsaert | 433/229 |
| 5,342,696 | 8/1994 | Eidenbenz et al. | 428/542.8 |

FOREIGN PATENT DOCUMENTS

| | | | |
|---|---|---|---|
| 0 160 797 | 11/1985 | European Pat. Off. | A61C 5/10 |
| 0 455 854 | 11/1991 | European Pat. Off. | A61C 13/00 |
| 0 480 209 | 4/1992 | European Pat. Off. | A61C 13/00 |
| 0 482 000 | 4/1992 | European Pat. Off. | A61C 13/08 |

OTHER PUBLICATIONS

Marks et al., J. Dent. Res. 75:148, Abstract 1041, 1996.
Mörmann et al. "CAD/CIM in Aesthetic Dentistry," CEREC 10 Year Anniversary Symposium, pp. 81–110, W.H. Mormann (Ed.), Quintessence Publishing Co., Inc., Chicago 1996.
"Cerec/Cerec 2, Vitablocs Mark II", VITA Zahnfabrik H. Rauter GmbH & Co., Sep. 1994.
"The New Epoch. Cerec 2", Siemens Aktiengesellschaft, Sep. 1994.

Primary Examiner—Deborah Jones
Assistant Examiner—Abraham Bahta
Attorney, Agent, or Firm—Marshall, O'Toole, Gerstein, Murray & Borun

[57] ABSTRACT

A blank for preparing artificial tooth parts, such as inlays, overlays or partial and complete crowns and bridges comprises a body of laminate material. The body has at least one layer of high abrasive resistance, at least one layer of high breaking strength, and at least one layer of lower hardness and breaking strength. For forming the tooth part, material is removed from the blank in such a way that the layer having high fracture strength forms a reinforcing structure. In a single working step, a tooth part of high strength can be machined.

18 Claims, 5 Drawing Sheets

METHOD FOR THE MANUFACTURE OF DENTAL RECONSTRUCTIONS AND BLANK FOR CARRYING OUT THIS METHOD

CROSS REFERENCE TO RELATED APPLICATIONS

This application claims the priority of the Swiss application 1251/96, filed May 17, 1996, the disclosure of which is incorporated herein by reference in its entirety.

BACKGROUND OF THE INVENTION

The invention relates to a blank and a method for preparing artificial tooth parts as well as a method manufacturing the blank.

The preparation of dental reconstructions, such as crowns or bridges, is usually carried out in the dental laboratory because prostheses having the required stability can only be prepared by combining a strong, load carrying material and weaker veneering materials, which requires several manufacturing steps. Such reconstructions are difficult to prepare.

The conventional state of the art method is the preparation of dental reconstruction bodies from a compound material, especially in the form of the porcelain fused to metal (PFM) reconstruction. In this method a supporting basic structure of metal is fitted, using a cast technique, to a tooth model obtained by dental preparation. The shape and color of the tooth are then added by burning ceramic material manually onto the basic structure. The combination of the highly tensile carrier material with a finish defining the color has proved to be successful as a durable method of reconstruction.

Lately, manual (Celay) and computer controlled (Cerec and other) methods have become known, by means of which dental reconstructions and parts of reconstructions can be prepared by grinding blanks out of single phase porcelain and ceramic material or polymer and composite material in a single step process, see e.g. W. H. Mormann, M. Brandestini, "Die CEREC Computer Reconstruction", 1989, Quintessenz Verlags-GmbH, Berlin, ISBN 3-87652-550-0. For example, blanks of feldspathic porcelain are used in the Cerec technique for producing inlays, onlays and veneers, as described in EP 160 797 A.

In a different method as described in EP 482 000 A, color layered blocks of plastic are suggested for preparing complete artificial teeth by abrasive machining using the Hennson/Sopha CAD/CAM-grinding technique. The prefabricated layer arrangement is selectively removed using reference information. Other grinding and milling techniques mainly prepare metal copings and parts of bridges for subsequent veneering with ceramics (DCS). These restaurations are designed for macromechanical retention and can be incorporated conventionally using zinc phosphate cement.

In an other method alumina blanks of porously sintered aluminum oxide or spinell ceramics respectively are shaped using the Cerec or Celay grinding techniques. The resulting shaped parts with open porous structure are then hot infiltrated (In-Ceram technique) with glass (lanthanum glasses), whereby a stability suitable for crowns and bridges is achieved.

The methods for manufacturing artificial tooth parts mentioned so far require a plurality of steps for preparing crowns or bridges, i.e. extra-coronal reconstructions, because these consist of at least two materials, one of which guarantees solidity and an other, weaker provides the natural dental color.

BRIEF SUMMARY OF THE INVENTION

Hence, it is a general object of the invention to provide a method and a blank for easily preparing ready-to-use crowns and bridges and other partial tooth reconstructions with good mechanical properties.

Now, in order to implement these and still further objects of the invention, which will become more readily apparent as the description proceeds, the blank is manifested by the features that it comprises a body for being shaped by material removal and a holder means for mounting the blank in a known position in a shaping apparatus, wherein the body comprises a reinforcing section and a bulk section, wherein the reinforcing section has a higher fracture strength than the bulk section The fracture strength (sometimes also termed breaking strength) designates the force or tension required for breaking a material.

In an other aspect of the invention, it relates to a method for manufacturing an artificial tooth part from a blank, said blank comprising a reinforcing section and a bulk section, wherein said reinforcing section has a higher fracture strength than said bulk section, said method comprising a material removal step of removing material from said blank such that said reinforcing section forms a reinforcing structure in an occlusal area of said artificial tooth part.

The invention also relates to a method for manufacturing a blank comprising a body for being shaped by material removal, wherein said body comprises a reinforcing section and a bulk section, said reinforcing section having a higher fracture strength than the bulk section, said method comprising the step of joining said bulk section and said reinforcing section as layers for forming said body by lamination.

Because the blank according to the invention comprises areas of different fracture strength, the final product can be shaped in one single machining step by material removal. In the artificial tooth part prepared in this way, the reinforcing section provides the necessary mechanical stability, while the bulk section can consist of a material that can be machined easily and/or the properties of which (elasticity, structure, color) can be adapted to the specific requirements.

The reinforcing section should preferably be arranged in a predefined spatial relation in respect to the holder means of the blank. This makes the position of the reinforcing section in the working tool known, and it becomes possible, while shaping the reconstruction, to make sure that the reinforcing section retains at least a required minimum thickness in the strongly stressed occlusal parts of the reconstruction. In particular, the reinforcing section of a dental crown should have an occlusal thickness of at least 0.5 mm.

Preferably, the reinforcing section is a substantially flat plate. Surprisingly, such a simple reinforcing section provides sufficient reinforcement. In a preferred embodiment the body comprises several laminate layers, which are preferably flat. This further simplifies the preparation of the blank. However, bent layers, e.g. cylindrical or spherical layers, are conceivable as well.

The reinforcing section is best located between a masticative section and the bulk section. The masticative section has a higher resistance against masticative abrasion, and the reinforcing section allows a good distribution of the masticative forces, while the remaining bulk section substantially serves for fitting the residual tooth and completing its shape. In this way a reconstruction can be prepared the occlusal side of which has a resistance to masticative abrasion and a breaking strength adapted to the biological requirements, while the other parts can e.g. be optimized for good workability.

The bulk portion of the body of the blank should preferably be made from ceramics, composite material, glasses and/or highly solid polymer materials. These materials can be prepared having tooth colors such that the individual sections can extend to the surface of the dental reconstruction.

The blank according to the invention is especially suited for the preparation of inlays, overlays, partial or complete crowns and bridges, i.e. parts of a tooth or complete teeth. Even though these parts can be quite thin and delicate, the required strength and elastic properties of the reconstruction can be achieved by suitable positioning and shaping of the reinforcing section.

BRIEF DESCRIPTION OF THE DRAWINGS

The invention will be better understood and objects other than those set forth above will become apparent when consideration is given to the following detailed description thereof. Such description makes reference to the annexed drawings, wherein.

DETAILED DESCRIPTION OF THE INVENTION

In the following, the steps for preparing a blank according to the invention and its processing are described briefly. Then, some specific embodiments of the blank are discussed.

Figure 1:
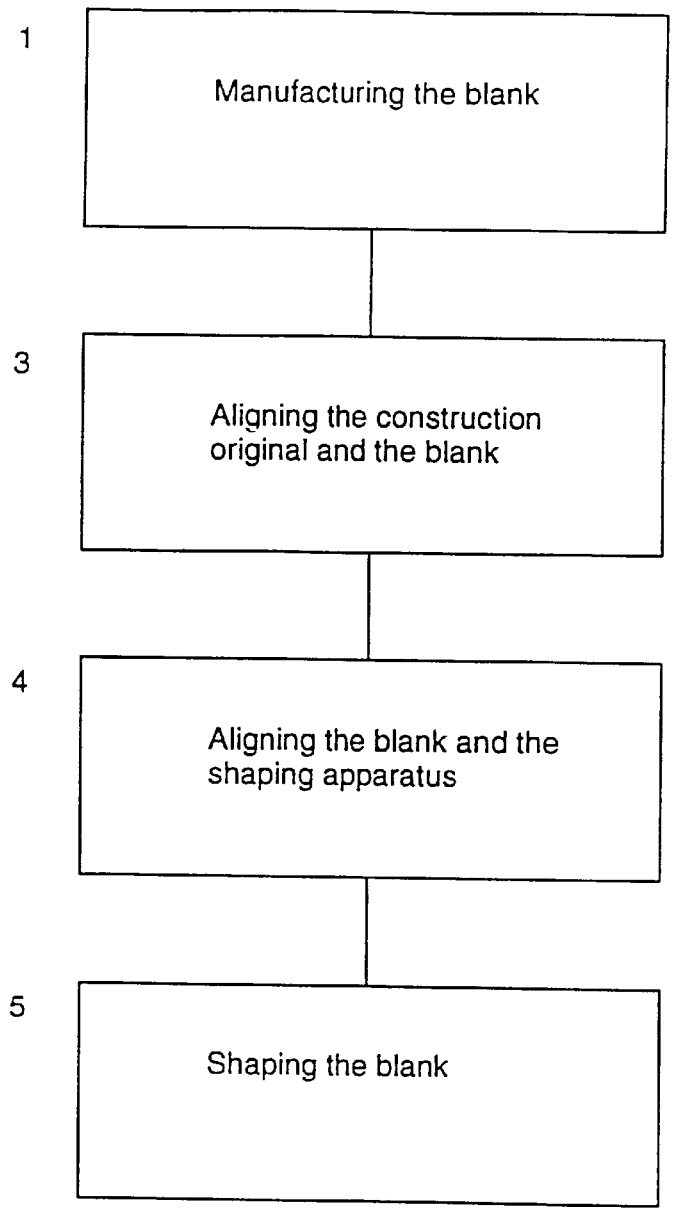
FIG. 1 is a flow chart depicting the manufacturing of a blank and its shaping.

FIG. 1 shows the steps during preparation of the blank and its subsequent shaping into a dental reconstruction.

In step 1, the blank is prepared industrially. The purpose of this step is the preparation of a blank having a section with optimum masticative properties, a section of high fracture strength, and a section of more resilient, well workable material. In the completed restoration, material of the section of high fracture strength will form a reinforcing zone for providing the required mechanical stability.

The blank can be manufactured in different ways, two of which are to be described now.

Figure 4:
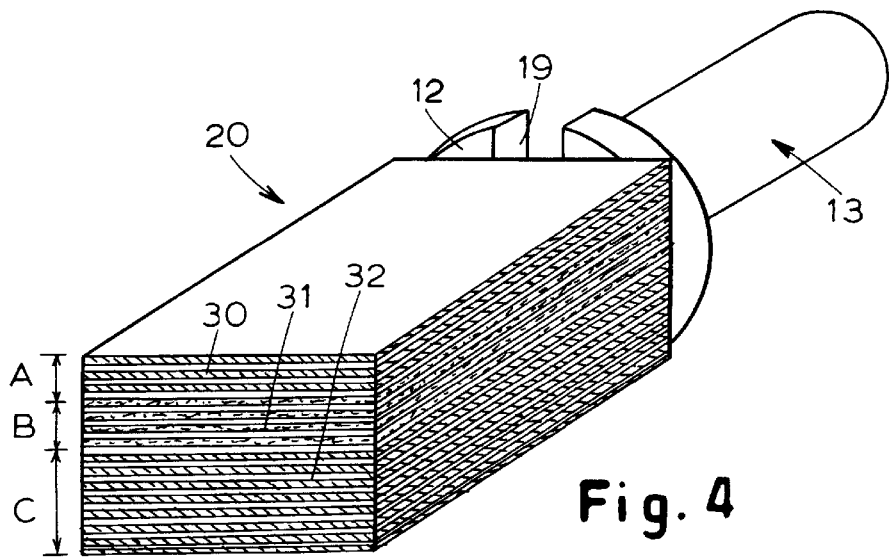
FIG. 4 is a second embodiment of a complete blank.

In a first, preferred method of preparation, a blank as e.g. shown in FIG. 4 is built layer by layer from prefabricated, planar layers or laminates of composite and or ceramics, glass, carbon or other suited materials. The layers can either be connected by means of an adhesive, e.g. by using composite as a glue, or ceramic laminates can be connected by means of firing or in a coating process. Also, layers of open-porous ceramics of equal or different pore structure can be connected by means of polymers. In this case, the polymer enters, on the one hand, the pores, on the other hand it forms a connection between the individual layers. (For the technique of open-porous, polymer treated ceramics, we refer to Marks et al., J. Dent. Res. 75: 148 Abstr. No 1041, 1996.) The layer thickness is chosen according to the desired mechanical and optical properties and ranges between less than one micrometer and several millimeters. In a most simple form one half of the blank is formed by a ceramic layer, the other half by a composite layer, wherein one of the layers forms the reinforcing section. However, it is also conceivable that layers of composite and ceramic of different construction and composition are used, wherein the reinforcement is provided by special material properties. The reinforcement can also be based on a specific arrangement of layers, on the thickness of the laminates, on a combination or group of laminates, or on combination of such elements. It is also conceivable to use ceramics of different thermal expansion coefficients for preparing the blank. The mechanical strain induced in this way strengthens the layers and increases the breaking strength.

This method of preparation allows the prefabrication of the individual layers, which allows a better quality control as compared to the preparation of monophase crown blanks with dimensions of e.g. 12×14×18 mm. Building the blank layer by layer avoids the problems of pore or flaw formation encountered when preparing large mono-phase bodies.

Figure 3:
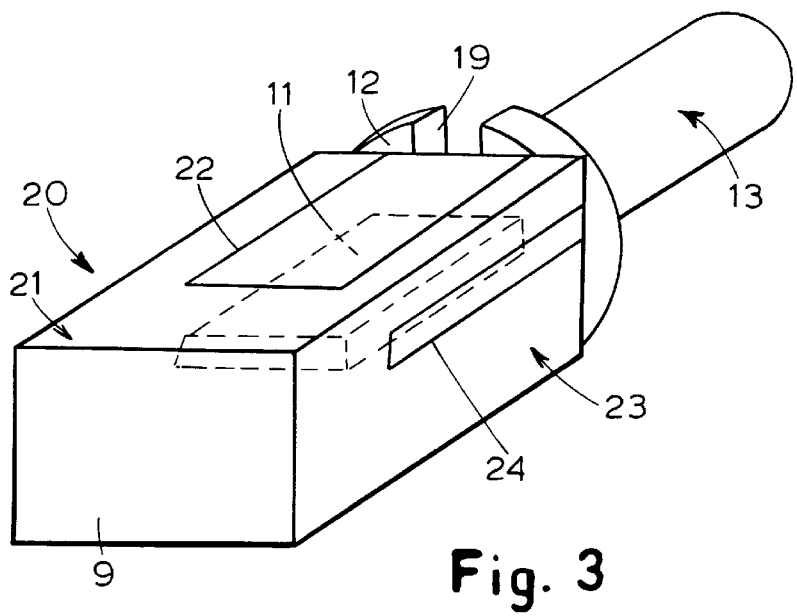
FIG. 3 is a first embodiment of a complete compound blank with the first variant of the reinforcing section of FIG. 2 in perspective view.

In a second possible method of manufacture, a blank, e.g. as shown in FIG. 3, is prepared in at least two steps. In a first step, the reinforcing section of a material of high fracture strength is prepared, which, in a second step, is completed to a compound blank by adding suitably colored and/or easily workable material. Prefabrication of the reinforcing section can e.g. be carried out by molding, drossing, hot pressing, or dry pressing and sintering, extrusion or material removal. The dimensions of the reinforcing section are chosen to match a typical restoration size. Preferred reinforcing materials are densely sintered ceramics or aluminum oxide, zirconium oxide, magnesium oxide, silicon oxide or combinations thereof, or high strength polymer. Metal can be used if the reinforcing section does not extend to the surface of the completed reconstruction. In this case, titanium is preferred among the metals. After manufacturing the reinforcing section, softer material is added to form the blank, either without special previous treatment, or with a treatment of the reinforcing section by adding or forming an adhesive intermediate layer thereon. The completion of the reinforcing section to an integral blank is carried out by heat and/or pressure polymerization, hot pressing or dry pressing and sintering or firing. The blank prepared in this way has the size of a typical restoration and can be shaped by material removal. However, it is also possible to prepare the different sections of the blank in parallel, e.g. by co-extrusion of differing ceramic masses with subsequent firing. Furthermore, it is also conceivable to add ceramic layers in a dipping process or using plasma sputtering.

Regardless of the method of preparation, the reinforcing section is preferably arranged such that the mesio-distal axis of the part of the blank intended to form the inner part of the masticative region of the restoration substantially coincides with the central axis of rotation of the blank.

The blank must be provided with suitable means for attachment and orientation, which allow to mount the blank in a grinding apparatus in such a way that the position of the reinforcing section is known. The means of orientation can be connected directly to the reinforcing section or they can be attached to the complete compound blank.

After step 1 of FIG. 1 the blank is completed. The remaining steps 3–5 of FIG. 1 can be carried out by the dentist, who will first prepare the tooth such that the shape of the desired reconstruction, the "construction original" is known.

Step 3 establishes the spatial orientation of the construction original in respect to the blank. For this purpose, the spatial contours of the reinforcing section of the composite blank are arranged such that they coincide with the desired support structure in the occlusal face. The orientation must be such that at least part of the reinforcing section remains intact after the shaping process in order to form the reinforcement of the reconstruction. The spatial orientation is either carried out in respect to a manually prepared provisional reconstruction (e.g. a plastic crown) or in respect to a digitized data set (e.g. optically obtained three dimensional image data, "optical impression"). There are different methods to do this, which can be used individually or, some of them, in combination:

a) For an approximate alignment, marker lines can be applied to the surface of the blank for indicating the orientation of the reinforcing section. These lines can be used for aligning the blank in a grinding apparatus.

b) When an optical impression is prepared, the camera is aligned to the mesio-distal axis of the teeth. The data set obtained in this way defines the grinding axis along the row of the teeth. It is also possible to overlay the contours of the reinforcing section and the contours of the blank in a video picture of the camera, wherein the camera is then aligned such that the reinforcing section coincides at least partially with the desired reinforcing structure in the reconstruction.

c) The spatial alignment of optically obtained three dimensional image data to the blank is carried out automatically using image overlay techniques. Suitable matching algorithms are used for orienting the spatial position of the blank and its reinforcing section with respect to the desired reconstruction such that the reinforcing section forms the desired reinforcement in the reconstruction.

Step 4 of FIG. 1 consists of the spatial alignment of the composite body and its reinforcing section in respect to the shaping apparatus. For this purpose, the reinforcing section must be brought into a known position within the apparatus. For example, the longitudinal axis of the reinforcing section can be placed into the rotational axis of a grinding tool, while the angular position is defined by a stop on the holder of the blank. For this purpose, an orientation help is provided on the holder of the blank, which makes it possible to establish the spatial relationship between the apparatus and the reinforcing section. The orientation help can e.g. comprise:

a) a continuous extension of the reinforcing section shaped as a holder having reference surfaces outside the blank;

b) a separately prepared holder, which is connected to the reinforcing section in a form locking manner;

c) a separately prepared holder, which is connected to the blank, wherein the relative position of the holder in respect to the reinforcing section is known, e.g. by aligning the longitudinal rotational axis of the reinforcing section with the one of the holder.

In step 5 of FIG. 1 the blank is then shaped using conventional techniques, preferably grinding. Most of the material is removed from the bulk section and part of it from the reinforcing and/or masticative section of the blank. The blank is preferably arranged such that the distal face of the reconstruction is arranged on the side of the holder because this side will be invisible once the prosthesis is positioned in the patient's mouth.

The reinforcing section should have at least a thickness of 0.5 mm in the occlusal region of the fully shaped restoration.

Figure 2:
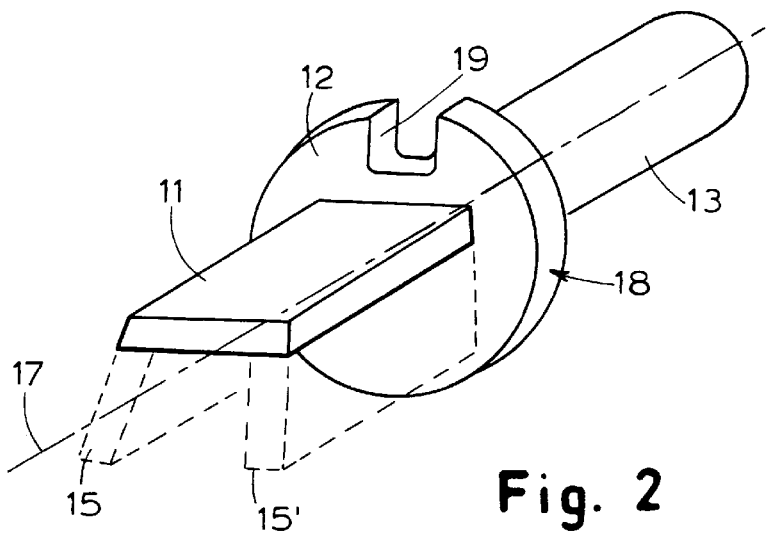
FIG. 2 is a first variant of the reinforcing section in perspective view.

FIG. 2 shows a first embodiment of the blank, wherein only the reinforcing section but not the bulk section are shown. In this embodiment, the reinforcing section 11 has the shape of a flat plate. This plate is connected to a holder comprising a calibration section 12 and a shaft 13.

The reinforcing section preferably is shaped such that the subsequent removal of material therefrom is minimized, which, in FIG. 2, is achieved by making the area a thin plate with a thickness between 0.5 and 3.0 mm. In the completely shaped reconstruction, e.g. a crown, the reinforcing section is located in the masticative region. Preferably, it is arranged close to the axis 17 of the blank but somewhat outside its center.

The reinforcing section 11 can also be a U-shaped profile with a longitudinal axis parallel to axis 17 of the blank and an opening angle of the legs of approximately 10°. The legs 15, 15' of such a profile are indicated by dotted lines in FIG. 2. The U-shape is similar to the shape of a crown on a conical tooth core and provides an additional lateral reinforcement of the reconstruction, without requiring a large amount of hard reinforcing material, thereby avoiding unnecessary wear of the tools. The reinforcing section can also be bent and/or have the shape of an L-profile.

Calibration section 12 of the holding means has a rotationally symmetric cylindrical shape and is finished with low tolerance. Its outer surface 18 is used as a reference surface, which can be contacted by the tools for calibration. A recess 19 provides the angular orientation, i.e. it makes sure that the reinforcing section can also be mounted in a single position. Therefore, the cylindrical surface 18 and recess 19 provide a means for orienting the reinforcing section 11 in a known position in respect to the shaping apparatus.

Shaft 13 has a substantially rotational symmetric shape, which defines the center of rotation of the blank in the shaping apparatus. The apparatus is provided with a suitable chuck or clamp for holding shaft 13. Shaft 13 can also be used for holding the blank during manufacturing while material is added onto the reinforcing section.

In the present embodiment, shaft 13, calibration section 12 and reinforcing section 11 are directly connected to each other. The relative position of calibration section 12 and reinforcing section 11 should always be the same for the blanks of one type, such that the position of the reinforcing section can be derived from cylindrical surface 18 and recess 19.

FIG. 3 shows a first variant of a complete blank 20 with reinforcing section 11 according to FIG. 2. Together, bulk section 9 and reinforcing section 11 form the complete composite blank, which is to be shaped by removal of material.

On the occlusal side 21 of blank 20, which has the same orientation as recess 19, the occlusal contours 22 of the reinforcing section 11 are indicated by lines, while the lateral contours 24 are drawn on the lateral surface 23. These contours provide information on the orientation of reinforcing section 11 within blank 20.

FIG. 4 shows a second, presently preferred embodiment of a complete blank 20. It consists of a plurality of flat laminar layers, which are e.g. connected to each other by means of composite and/or polymer material. The layers 30 in a topmost region A of the blank are made from a material that has a high resistance against masticative abrasion, preferably a hard material. Layers 31 of a ceramic material with high fracture strength are arranged in an intermediate region B. Layers 32 of low hardness and strength, e.g. of composite, are arranged in a bottom most area C. Composite can be worked more easily than ceramics, such that the blank can be shaped more easily.

Region A forms a masticative section of the blank, from which the occlusal surface of the reconstruction is formed. Region B forms the reinforcing section, region C the bulk section.

Figure 10:
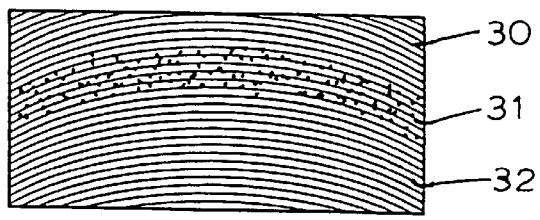
FIG. 10 is cross section of a third embodiment of the blank with bent layers.

In the blank of FIG. 4 the laminate layers are flat, which makes them easy to manufacture. However, as shown in FIG. 10, the layers 30–32 can also be bent, cylindrical or spherical, which improves strength and allows a better adaptation of the layers to the forces to be expected within the prosthesis.

Figure 5:
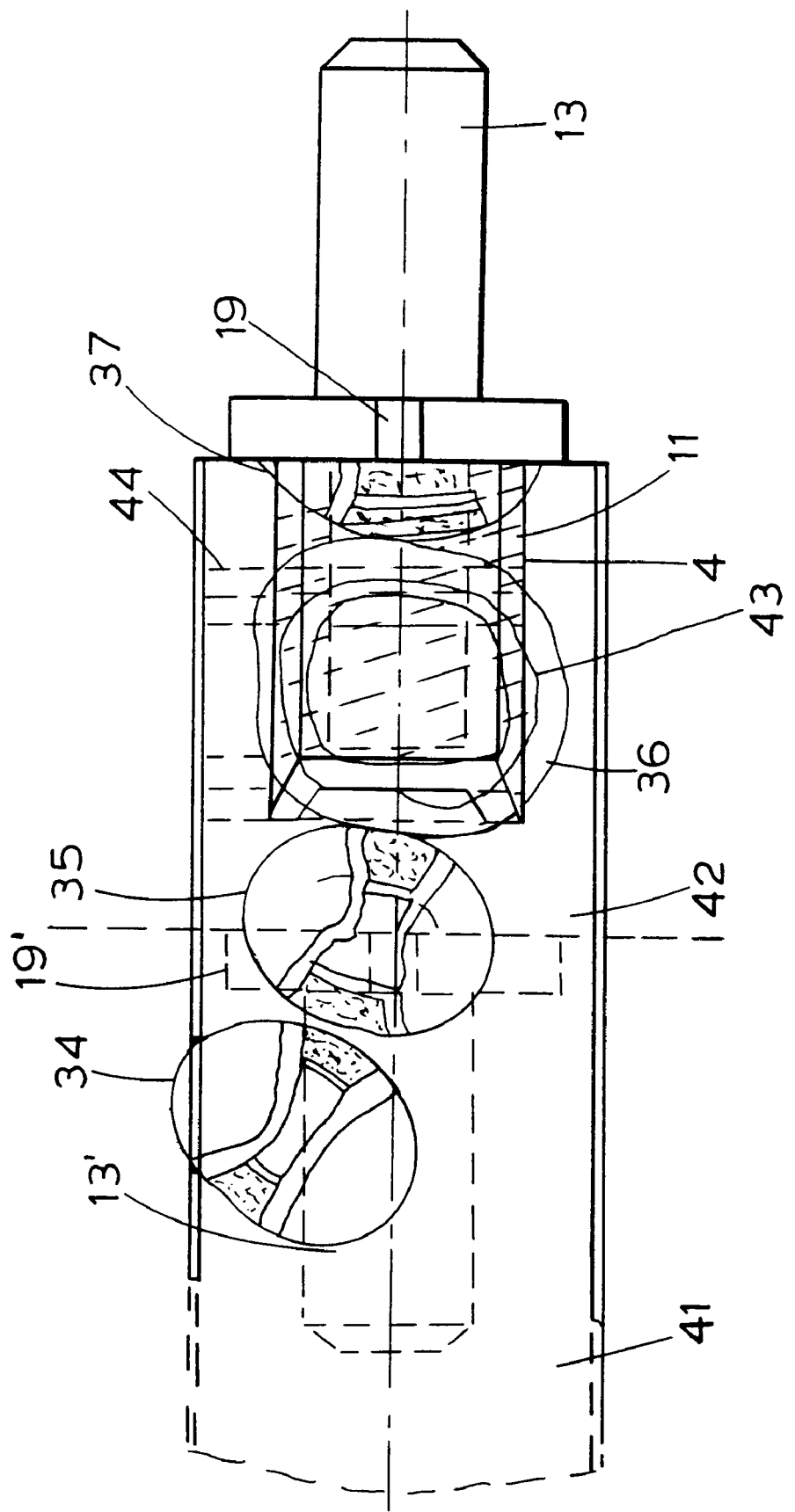
FIG. 5 shows the mesial and distal arrangement of the blank in relation to a crown preparation

FIG. 5 illustrates the orientation of a blank for working it. In this figure, a blank according to FIG. 2 with the U-shaped reinforcing section is shown—a corresponding alignment can, however, also be carried out with a blank having a flat reinforcing section (such as the one of FIG. 4), although the lateral position becomes less critical in this case.

FIG. 5 also shows the position of a three dimensionally measuring mouth camera with its shaft 41 and a recording window 42 in respect to a row of teeth 34–37. A corresponding mouth camera is e.g. described in H. Mörmann and M. Brandestini, "Die CEREC Computer Reconstruction", 1989, Quintessenz Verlangs-GmbH, Berlin, ISBN 3-87652-550-0. In the example of FIG. 5, tooth 36 is shaped into a cone 43 for receiving a crown. In its horizontal extensions, recording window 42 has approximately the size of a blank for molar crowns. With the help of contours of the reinforcing section 11, which are overlaid onto the camera image on the monitor while aligning the camera, it is possible to position the reinforcing section optimally onto cone 43. Shaft 13 with recess 19, which are also shown, illustrate the spatial relation of the whole blank in respect to the crown and tooth. Dotted shaft 13' and dotted recess 19' illustrate the spatial relation when using a blank as shown in FIG. 2, wherein lines 44 are the distal limit of the reinforcing section.

Figure 6:
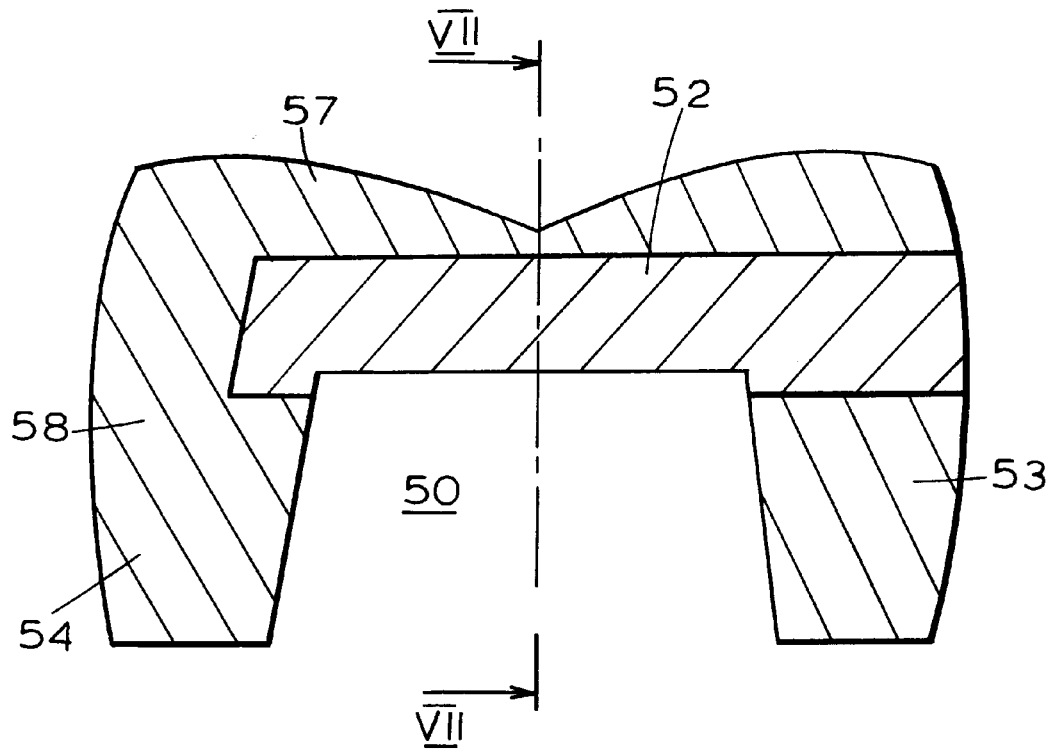
FIG. 6 is a schematic mesio-distal section through a crown prepared from the blank of FIG. 3.
Figure 7:
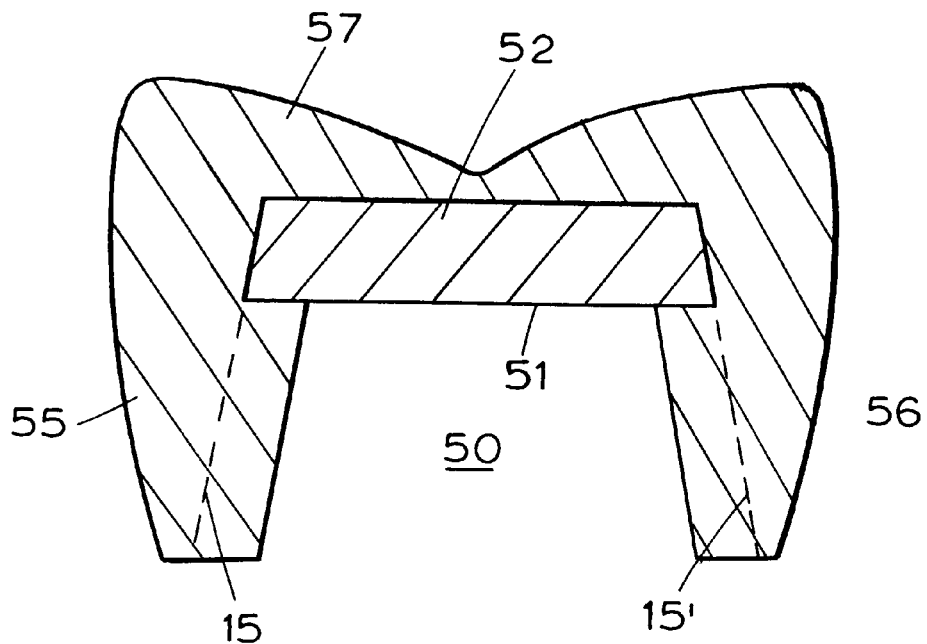
FIG. 7 is a section along line VII—VII of FIG. 6.

A completed molar crown prepared from the blank of FIG. 3 is shown in FIGS. 6 and 7. The crown has a conventional shape with a frustoconical recess 50 for receiving the tooth. The blank is shaped such that the reinforcing section forms a reinforcing plate 52 lying inside the blank in the occlusal region, where the largest strains occur. Plate 52 has a thickness of at least 0.5 mm.

If a U-shaped reinforcing section is used, as shown with dotted lines in FIG. 2, legs 15, 15' form reinforcements lying inside the buccal and oral lateral walls. The distal wall 53 of the crown consists in part of the shaft portion of the reinforcing section, while the mesial wall is only strengthened by the end portion of the reinforcing section. The outer surfaces of the mesial, oral, buccal and occlusal walls 54, 55, 56, 57 are formed by the bulk section of the blank.

Figure 8:
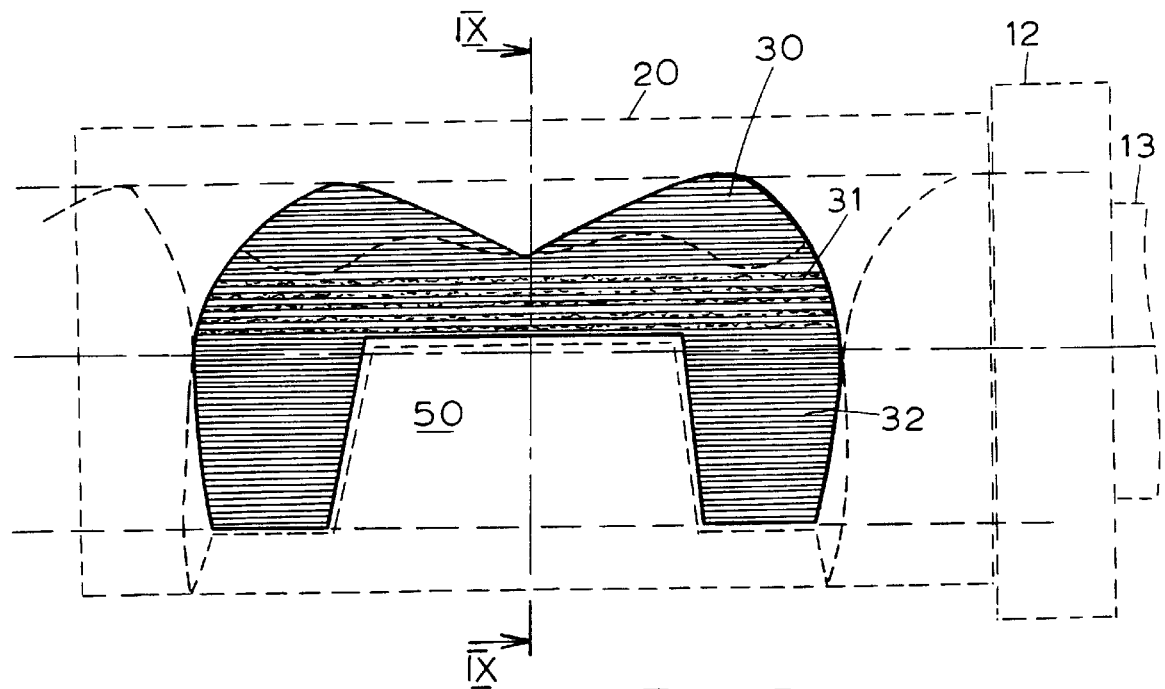
FIG. 8 is a schematic mesio-distal vertical section through a crown prepared from a laminated blank.
Figure 9:
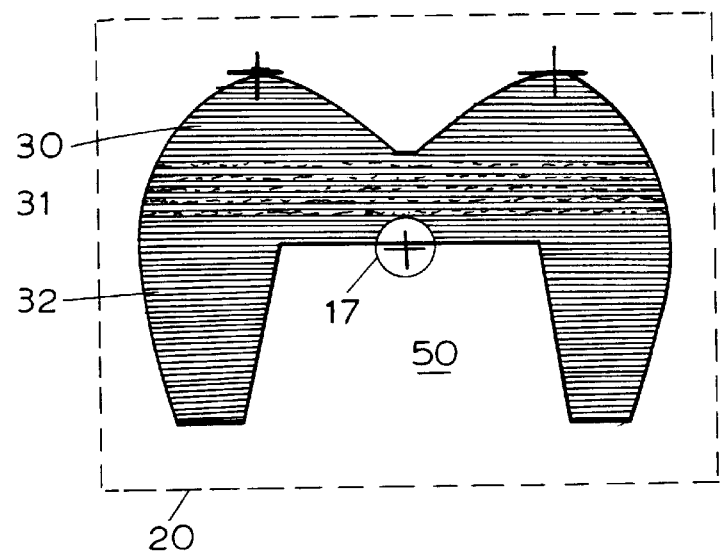
FIG. 9 is a section along line IX—IX of FIG. 8.

FIGS. 8 and 9 show a completed crown prepared from the laminated blank of FIG. 4, wherein the contours of the blank 20 and the holder means 12, 13 are shown with dotted lines. In this embodiment, the layers 31 of the reinforcing section form a reinforcing plate in the occlusal region of the reconstruction. The occlusal surface, which is very hard in a natural tooth, is formed by the layers 30 of the masticative section of the blank. The walls of the crown consists of the layers 32 of the bulk section. Because all layers 30, 31, 32 extend to the surface of the crown, they should have natural tooth color.

As it can be seen from FIGS. 6–9, most of the material to be ground off comes from the bulk section, some from the masticative section of the blank. Because the reinforcing section is somewhat offset from the center of the blank, only small portions of it must be removed, even in the area of recess 50. This decreases the time required for shaping the crown and reduces the wear of the tools.

In the embodiments shown so far, the blank consisted of two or three areas of different material: the reinforcing section, the bulk section and, in some embodiments, the masticative section. However, it is also possible that the blank consists of more than two or three materials. For instance, instead of clearly defined phase limits between the different sections of the blank, continuous gradients or finely graded steps can be used. In the laminated embodiment of FIG. 4, the individual laminate layers can e.g. become increasingly harder, stronger, more elastic or softer. The hardest laminate layers are preferably arranged in the topmost section of the blank. Below these hardest layers, stronger layers with higher fracture strength are used, which form the reinforcing section. Then follow the increasingly softer layers of the bulk section. Hence, following the example of a natural tooth, a continuos succession of abrasive-proof, rigid material at the top (ceramics) to more resilient material (e.g. composite) can be used, which improves the distribution of the strains and forces from the prosthesis onto the remaining tooth. In the region of the occlusal plateau, material with high breaking strength is used. The central and cervical areas are formed by material that can be shaped easily. The optical properties (color, translucence and X-ray opacity) of the layers can be adapted to the natural appearance of a tooth.

While there are shown and described presently preferred embodiments of the invention, it is to be distinctly understood that the invention is not limited thereto but may be otherwise variously embodied and practiced within the scope of the following claims.

I claim:

1. A blank for preparing an artificial tooth part, said blank comprising a body for being shaped by material removal and a holder means for mounting the blank in a shaping apparatus, wherein the body comprises a reinforcing section and a bulk section, wherein the reinforcing section has a higher fracture strength than the bulk section.

2. The blank of claim 1, wherein said reinforcing section is in a predefined spatial relation in respect to said holder means, such that said reinforcing section can be aligned by aligning said holder means.

3. The blank of claim 1 wherein said reinforcing section comprises at least one material selected from the group consisting of aluminum oxide, zirconium oxide, magnesium oxide, silicon oxide, and polymer.

4. The blank of claim 1 wherein said bulk section comprises at least one material selected from the group consisting of ceramics, glass, polymer and composites.

5. The blank of claim 1 wherein said reinforcing section is substantially a flat plate.

6. The blank of claim 5 wherein said plate extends through the whole body.

7. The blank of claim 5 wherein said reinforcing section has a thickness of at least 0.5 mm.

8. The blank of claim 1 wherein said body comprises a plurality of substantially flat laminate layers, wherein at least one of said laminate layers forms said reinforcing section.

9. The blank of claim 1 wherein said body comprises a plurality of bent laminate layers, wherein at least one laminate layer forms said reinforcing section.

10. The blank of claim 8 comprising a plurality of laminate layers having different thermal expansion coefficients.

11. The blank of claim 1 wherein said body further comprises a masticative section, wherein said reinforcing section is arranged between said masticative section and said bulk section, wherein said masticative section has a higher resistance to abrasion than said bulk section.

12. The blank of claim 11 wherein said reinforcing section has a higher fracture strength than said masticative section.

13. The blank of claim 1 wherein said body has a substantially symmetrical shape with a central axis and wherein said reinforcing section is laterally offset and said central axis is not a symmetry axis of said reinforcing section.

14. The blank of claim 1 wherein at least part of said sections of said body consist of ceramics comprising open pores, wherein a filling material is arranged in said pores and between said sections.

15. A blank for preparing an artificial tooth part, said blank comprising
- a body for being shaped by material removal and
- a holder means for mounting the blank in a shaping apparatus,
- wherein the body comprises a masticative section, a reinforcing section and a bulk section, wherein said reinforcing section has a higher fracture strength than said bulk section and wherein said masticative section has a higher resistance to abrasion than said bulk section.

16. The blank of claim 15, wherein said masticative section has a higher resistance to abrasion than said reinforcing section.

17. The blank of claim 15 wherein said reinforcing section has a higher fracture strength than said masticative section.

18. A blank for preparing an artificial tooth part, said blank comprising
- a holder means for mounting said blank in a shaping apparatus, and
- a body comprising a plurality of substantially flat laminate layers for being shaped by material removal, wherein said body comprises a reinforcing section formed by at least one of said laminate layers and a bulk section and wherein the reinforcing section has a higher fracture strength than the bulk section.

* * * * *